US00PP25171P3

(12) United States Plant Patent
Pierron-Darbonne

(10) Patent No.: US PP25,171 P3
(45) Date of Patent: Dec. 16, 2014

(54) RASPBERRY PLANT NAMED 'LUPITA'

(50) Latin Name: ***Rubus idaeus* L.**
Varietal Denomination: Lupita

(75) Inventor: Alexandre Pierron-Darbonne, Pamplona (ES)

(73) Assignee: Plantas de Navarra, S.A., Valtierra, Navarra (ES)

( * ) Notice: Subject to any disclaimer, the term of this patent is extended or adjusted under 35 U.S.C. 154(b) by 245 days.

(21) Appl. No.: 13/507,054

(22) Filed: May 30, 2012

(65) Prior Publication Data

US 2012/0311747 P1 Dec. 6, 2012

(30) Foreign Application Priority Data

Jun. 6, 2011 (QZ) ..... PBR 20111460

(51) Int. Cl.
*A01H 5/00* (2006.01)
*A01H 5/08* (2006.01)

(52) U.S. Cl.
CPC ..... *A01H 5/0887* (2013.01)
USPC ..... Plt./204

(58) Field of Classification Search
CPC ..... A01H 5/0887
USPC ..... Plt./204
See application file for complete search history.

*Primary Examiner* — Susan McCormick Ewoldt
*Assistant Examiner* — Louanne Krawczewicz Myer
(74) *Attorney, Agent, or Firm* — Christie, Parker & Hale, LLP

(57) ABSTRACT

The present invention relates to a new and distinct raspberry variety. The varietal denomination of the new variety is 'Lupita'. Among the characteristics which appear to distinguish the new variety from other varieties are a combination of traits which include a medium-sparse spines density and abundant production of light red colored, broad conical shaped, and big fruit size.

17 Drawing Sheets

Botanical classification: *Rubus idaeus* L.

Varietal denomination: The new plant has the varietal denomination 'Lupita'.

BACKGROUND OF THE INVENTION

The new variety of raspberry was created in a breeding program by crossing two parents; in particular, by crossing as seed parent an undistributed raspberry parent designated 07.09R.99 (unpatented) and as pollen parent an undistributed raspberry parent designated 07.13R.46 (unpatented). Female and male are selections from breeder's program of Planasa. Both parental varieties are property and have not been commercialized.

The resulting seedling of the new variety was grown and asexually propagated by roots cuttings in Segovia, Spain, 3° 59'W., 41° 22'N., 2742 feet elevation. Clones of the new variety were further asexually propagated and extensively tested. This propagation and testing has demonstrated that the combination of traits disclosed herein which characterize the new variety are fixed and retained true to type through successive generations of asexual reproduction.

SUMMARY OF THE INVENTION

The present invention relates to a new and distinct raspberry variety. The varietal denomination of the new variety is 'Lupita', that produces and maintains a strong vigorous plant with consistent fruit production from October through December on primocanes and in the ensuing year from ending April through begins June. Among the characteristics which appear to distinguish the new variety from other varieties are a combination of traits which include a medium-sparse spines density and abundant production of light red colored, broad conical shaped, and big fruit size.

COMPARISON NEW VARIETY TO CO-PENDING CULTIVAR 'ADELITA'

'ADELITA' shows a sparse spines density and a rigid spines texture; whereas 'LUPITA' shows a medium sparse spines density and a smooth spines texture.

'ADELITA''s leaf shows a free arrangement of lateral leaflets and the lateral leaftlets touching with the terminal leaflet; whereas 'LUPITA''s leaf shows a touching arrangement of lateral leaflets and the lateral leaflets do not touch with the terminal leaflet.

Fruit size of 'ADELITA' is bigger than fruit size of 'LUPITA'.

'ADELITA' shows a medium red fruit color, RHS red group color (near 47 A to 46 A), and 'LUPITA' shows a light red fruit color, RHS red group color (near 45 D to 46 B).

'ADELITA' shows a yield primocane bigger than 'LUPITA'.

COMPARISON NEW VARIETY TO THE PARENTS

The new variety is distinguished there from its parents by the following characteristics possessed by 'Lupita' which are different than, or not possessed, by the seed parent designated '07.09R.99' (unpatented) and the pollen parent designated '07.13R.46' (unpatented).

1. Pollen parent '07.13R.46' (unpatented) and seed parent '07.09R.99' are less vigorous than the plant of the new variety 'Lupita'.

2. In pollen parent '07.13R.46' (unpatented) the spines density is medium, whereas the new variety 'Lupita' presents a sparse density.
3. In seed parent '07.09R.99' (unpatented) the fruit size is smaller than in the new variety 'Lupita'.
4. In seed parent '07.09R.99' (unpatented) the fruit color is yellow, whereas in the new variety 'Lupita' is light red.

COMPARISON TO CLOSEST VARIETY

The new variety is closest to the variety 'Heritage' (Unpatented), but is distinguished therefrom by the following characteristics possessed by 'Lupita' which are different than, or not possessed by, 'Heritage'.

1. Plant habit in 'Heritage' (Unpatented) is upright whereas in 'Lupita' is arching.
2. Cane color in 'Heritage' is greyed purple (RHS greyed purple group near 185 C to 186 A), whereas in 'Lupita' it is a yellow green color (RHS yellow green group near 144 C to 144 B) with greyed red pigmentation (RHS greyed red group near 178 D to 178 C).
3. 'Heritage' exhibits a high spines density, whereas 'Lupita' shows a medium sparse spine density.
4. 'Heritage' shows a greyed red color (RHS greyed red group near 181 B to 181 A) of petiole, whereas 'Lupita' shows a yellow green color (RHS yellow green group near 144 C to 144 B) with greyed red pigmentation (RHS greyed red group near 178 D to 178 C).
5. Leaf green color of upper side in 'Heritage' is a yellow green color (RHS yellow green group near 147 A), whereas in 'Lupita' it is a green color (RHS green group near 137 B to 137 A).
6. 'Heritage' shows a fruit red purple colored (RHS red purple group near 59 A) with medium glossiness, whereas 'Lupita' shows a red color fruit (RHS red group near 45 D to 46 B) with strong glossiness.
7. General shape in lateral view of fruit of 'Heritage' is circular, whereas in 'Lupita' the general shape in lateral view of fruit is broad conical.

The differences in the color cane and spines density of 'Lupita' (designated 07.09R.52) and 'Heritage' (Unpatented) are shown in FIG. 8 and FIG. 14. The difference in the color petiole of 'Lupita' (designated 07.09R.52) and 'Heritage' (Unpatented) is shown in FIG. 7 and FIG. 15. The difference in the leaf color upperside of 'Lupita' (designated 07.09R.52) and 'Heritage' (Unpatented) is show in FIG. 3 and FIG. 16. The differences in fruit color and fruit shape of 'Lupita' (designated 07.09R.52) and 'Heritage' (Unpatented) are shown in FIG. 12 and FIG. 17. These differences are maintained during the harvest season.

PATENT STATUS OF PARENTAL CULTIVARS

The parental cultivars do not have any application for Plant Patent Rights in any country on the world.

Both parental cultivars have never been commercialized.

BRIEF DESCRIPTION OF ILLUSTRATIONS

The accompanying photographs show typical specimens of the new variety, designated 07.09R.52 in the illustrations, including fruit, foliage and flower, in color as nearly true as it is reasonably possible to make in color illustrations of this character.

The plants depicted in the drawings were planted Jun. 20, 2011 in the farm of La Mogalla in Cartaya (Huelva), Spain, about 7° W, 37° N, 45 feet elevation.

Drawings were taken December, 2011 (about Dec. 10 and Dec. 30, 2011): minimum temperate about 5° to 6° Centigrade, maximum temperate about 18 to 22° Centigrade.

FIG. 1 and FIG. 2 shows several plants of the new variety (designated 07.09R.52) which exhibit a upright habit plant with several red colored and broad conical shape fruits.

FIG. 3 and FIG. 4 show the upperside and the underside, respectively, of a complete leaf of the new variety (designated 07.09R.52). FIG. 3 shows that the leaf color of the upper side of the new variety (designated 07.09R.52) is RHS green group color (near 137 B to 137 A) and FIG. 4 shows the leaf color of underside of the new variety (designated 07.09R.52) is RHS green group color (near 139 B to 136 C).

FIG. 5 and FIG. 6 show the upperside and the underside, respectively, of terminal leaflet of the new variety (designated 07.09R.52). FIG. 5 shows that the leaf color of the upper side of the new variety (designated 07.09R.52) is RHS green group color (near 137 B to 137 A) and FIG. 6 shows that the leaf color of underside of the new variety (designated 07.09R.52) is RHS green group color (near 139 B to 136 C).

FIG. 7 shows the petiole of the new variety (designated 07.09R.52) with medium sparse spines density and two horizontal and narrow stipules.

FIG. 8 shows the color cane of the new variety (designed 07.09R.52) RHS yellow green group (near 144 C to 144 B) with RHS greyed red group pigmentation (near 178 D to 178 C). The spines density is medium sparse.

DESCRIPTION OF THE NEW VARIETY

Figure 1:
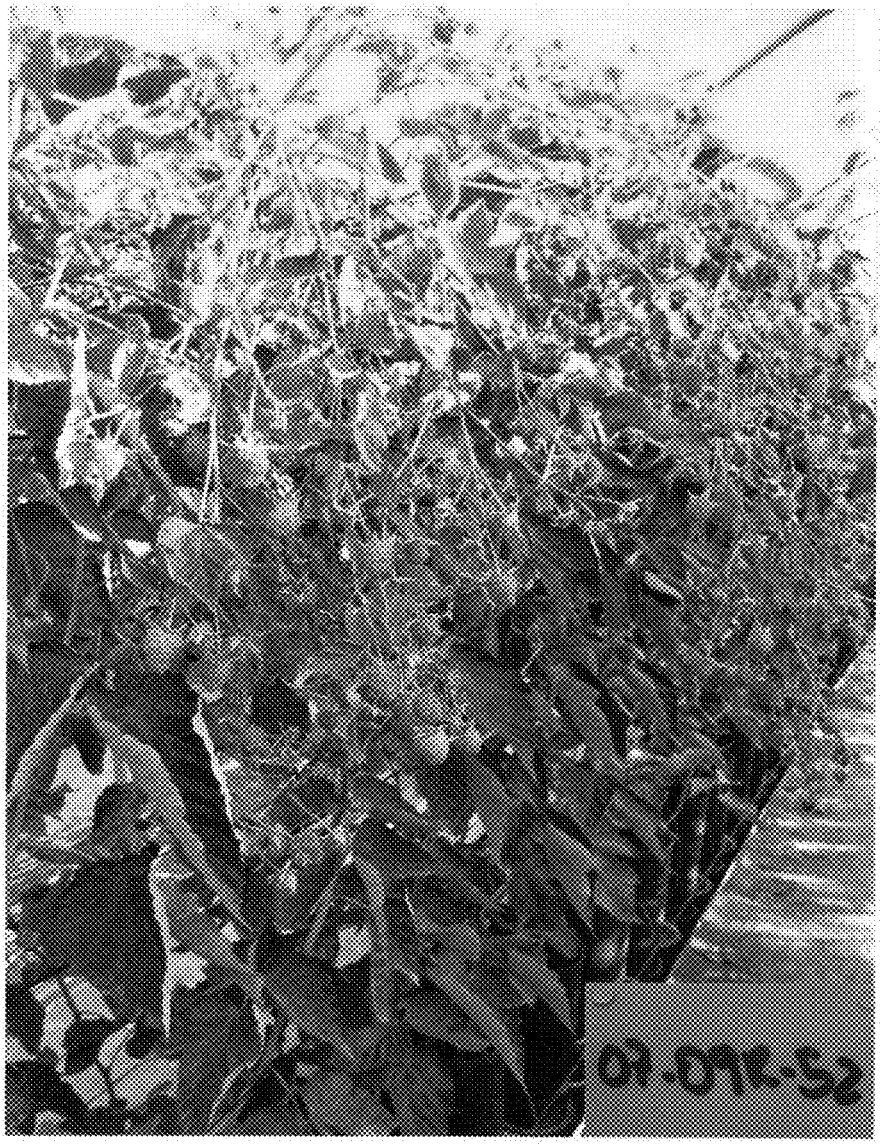
Figure 2:
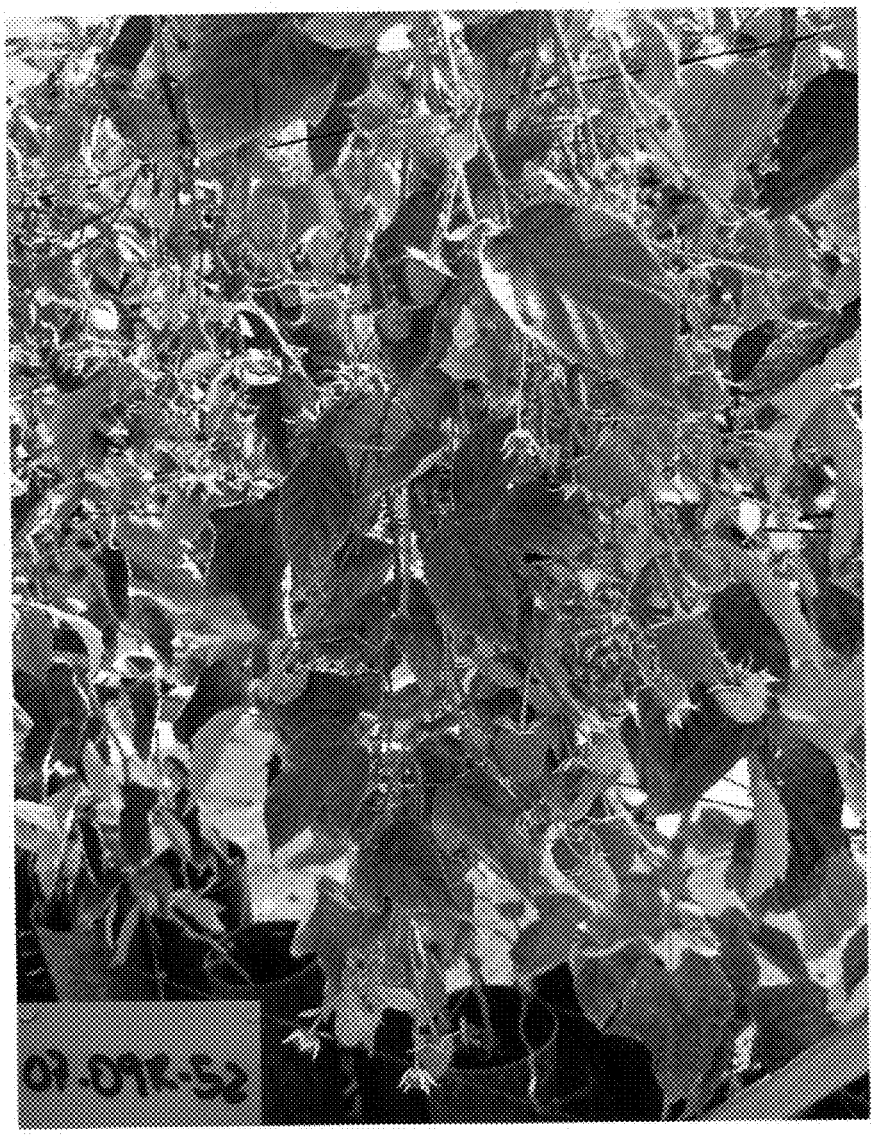
Figure 3:
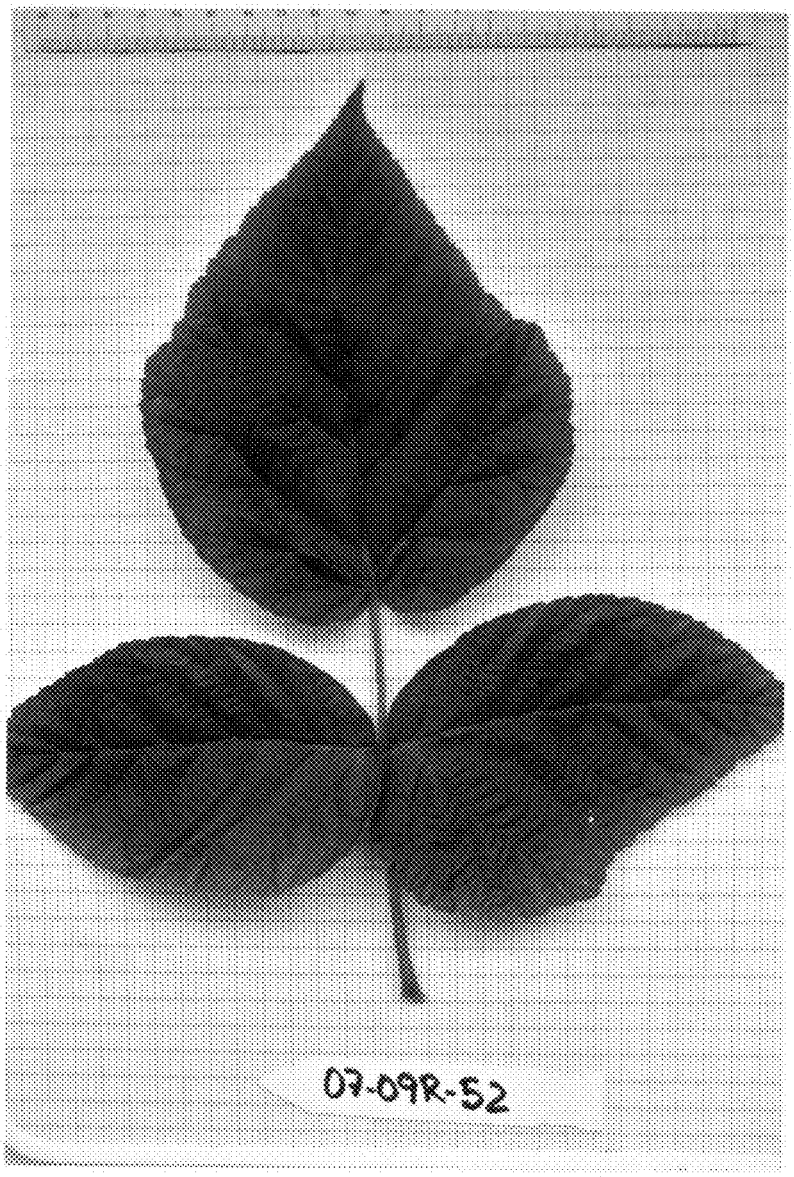
Figure 4:
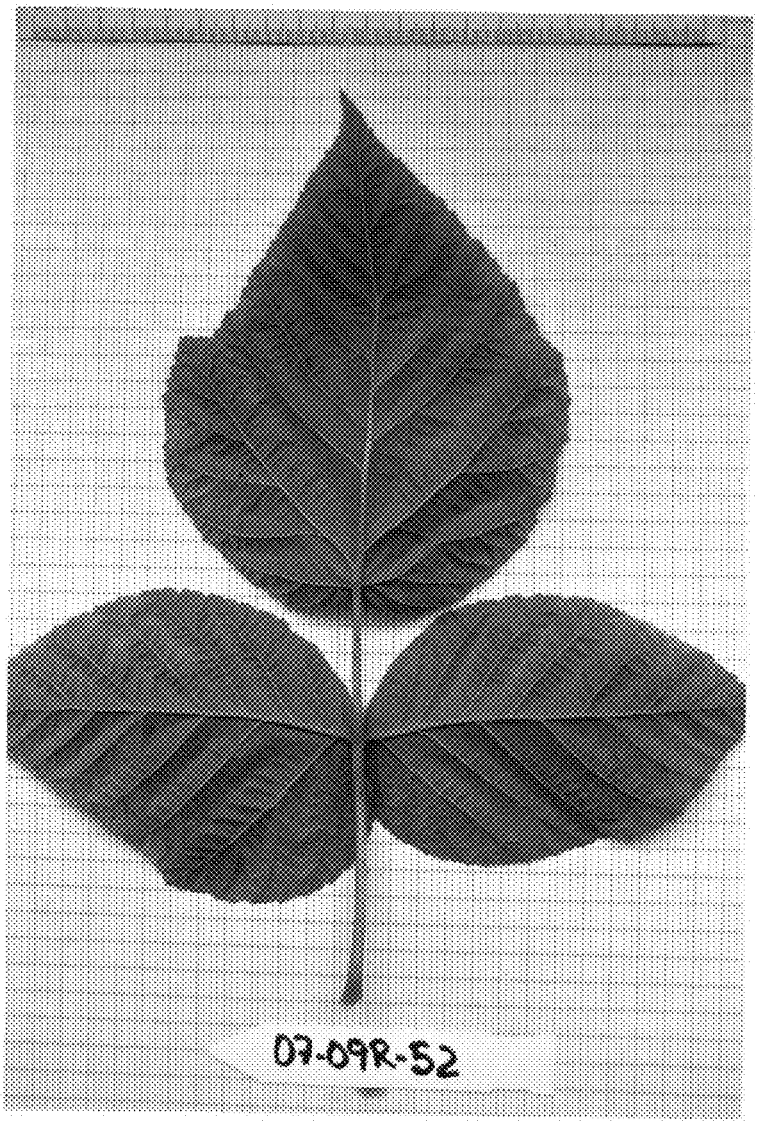
Figure 5:
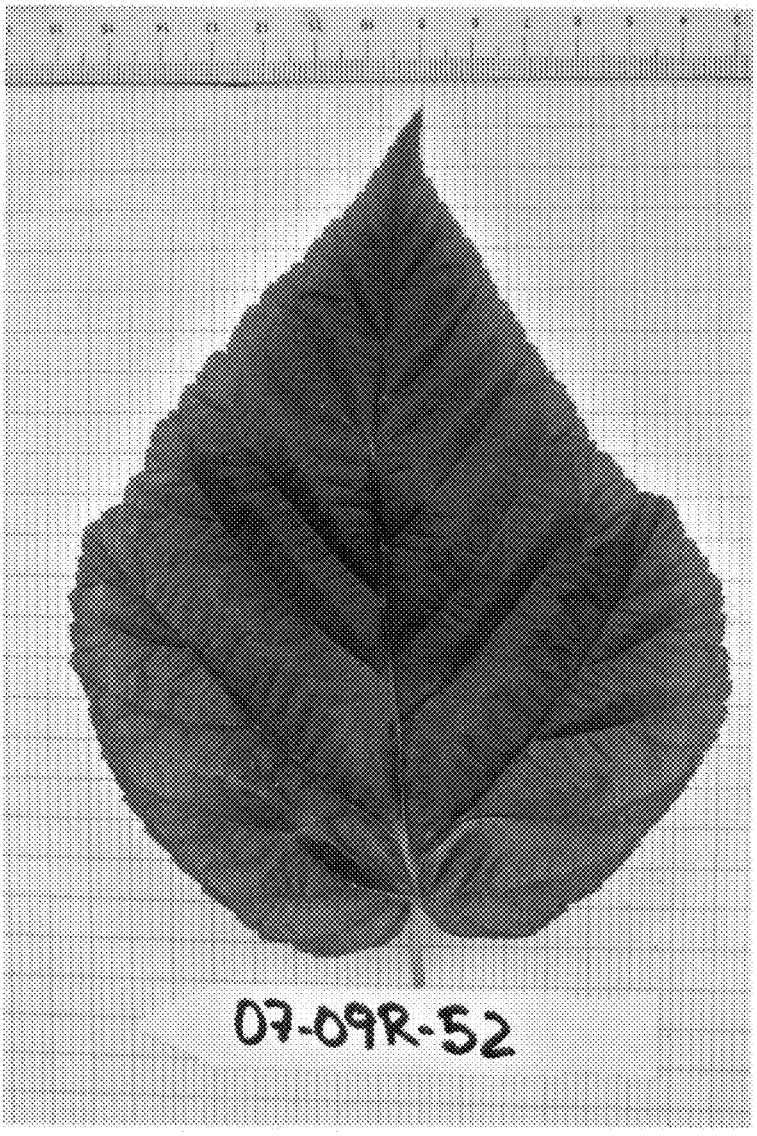
Figure 6:
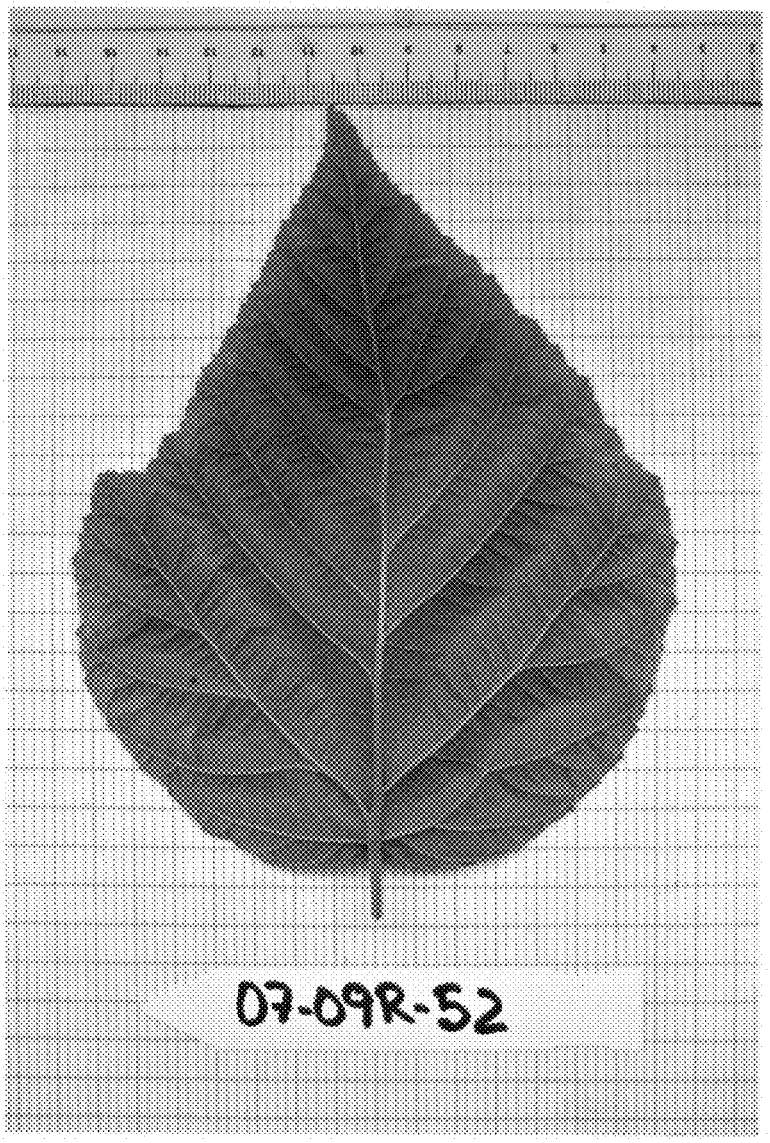
Figure 7:
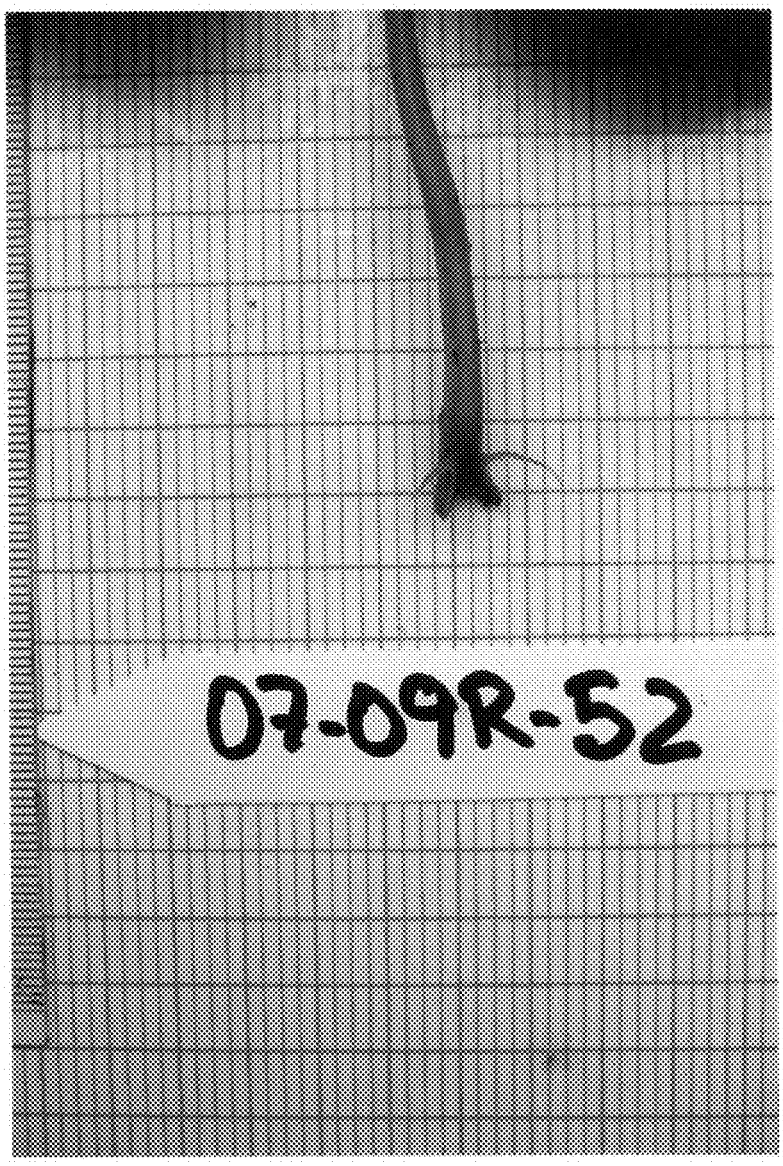
Figure 8:
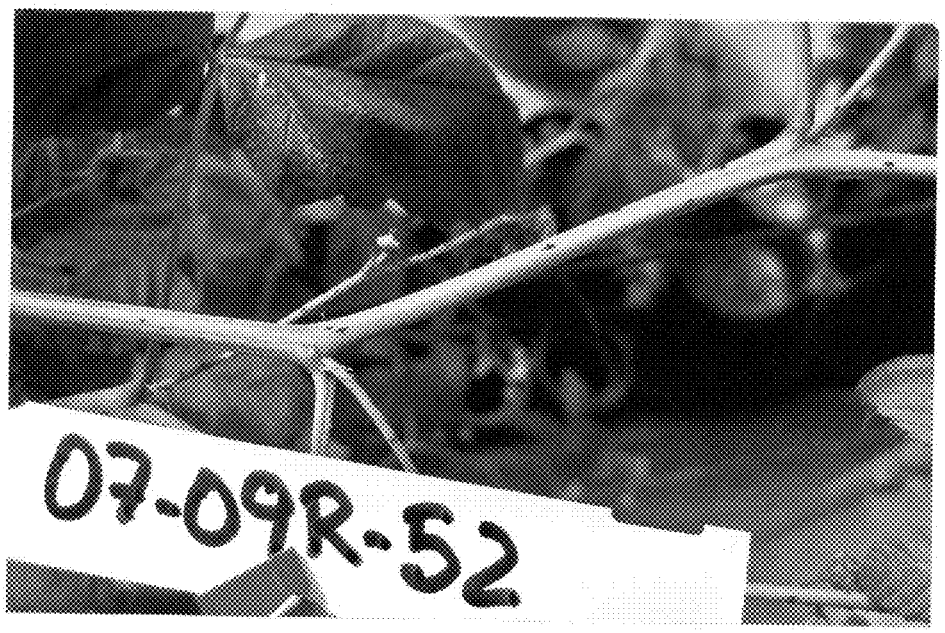
Figure 9:
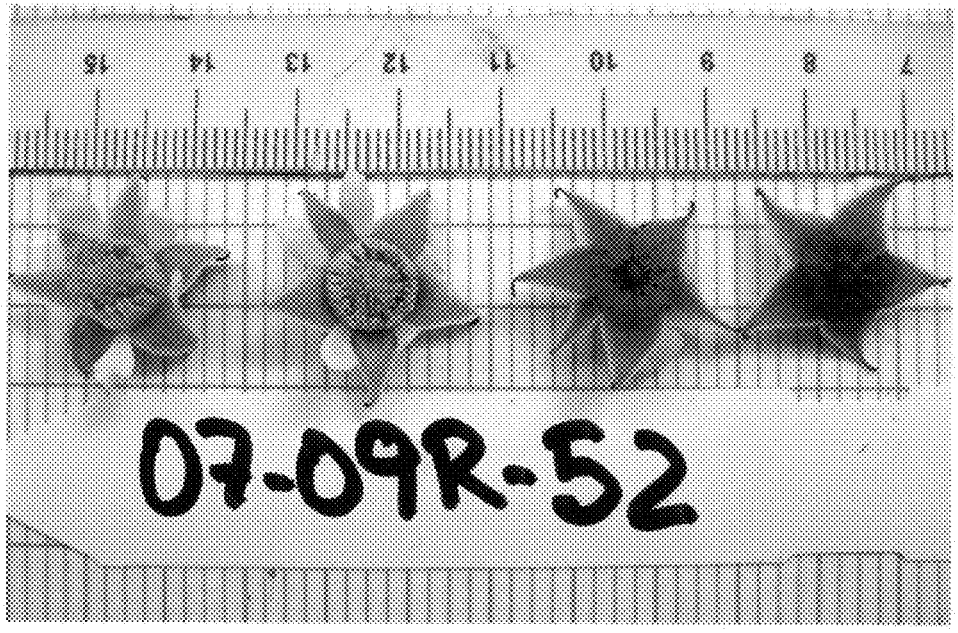
FIG. 9 shows typical flowers of the new variety (designated 07.09R.52).
Figure 10:
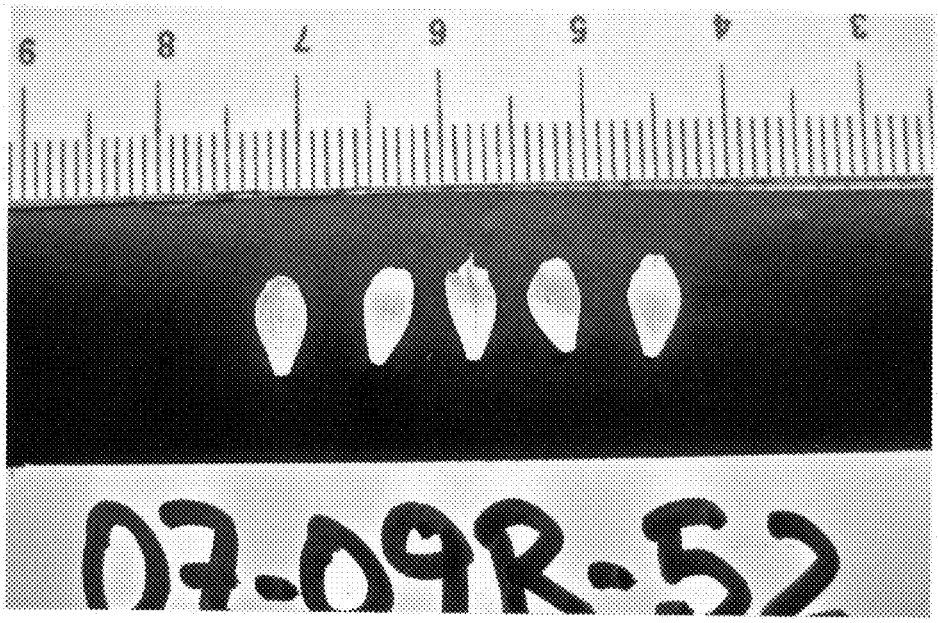
FIG. 10 shows typical petals of the new variety (designated 07.09R.52) with narrow elliptique shape and RHS white group color (near 155C).
Figure 11:
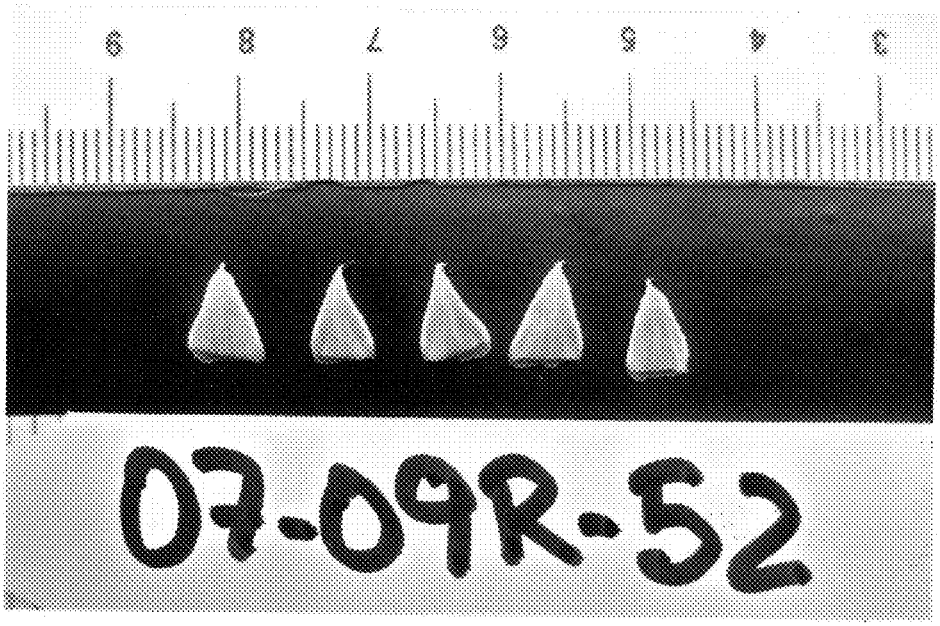
FIG. 11 shows typical sepals of the new variety (designated 07.09R.52) with triangular shape, acuminate apex and RHS green group color (near 142 D to 142 C).
Figure 12:
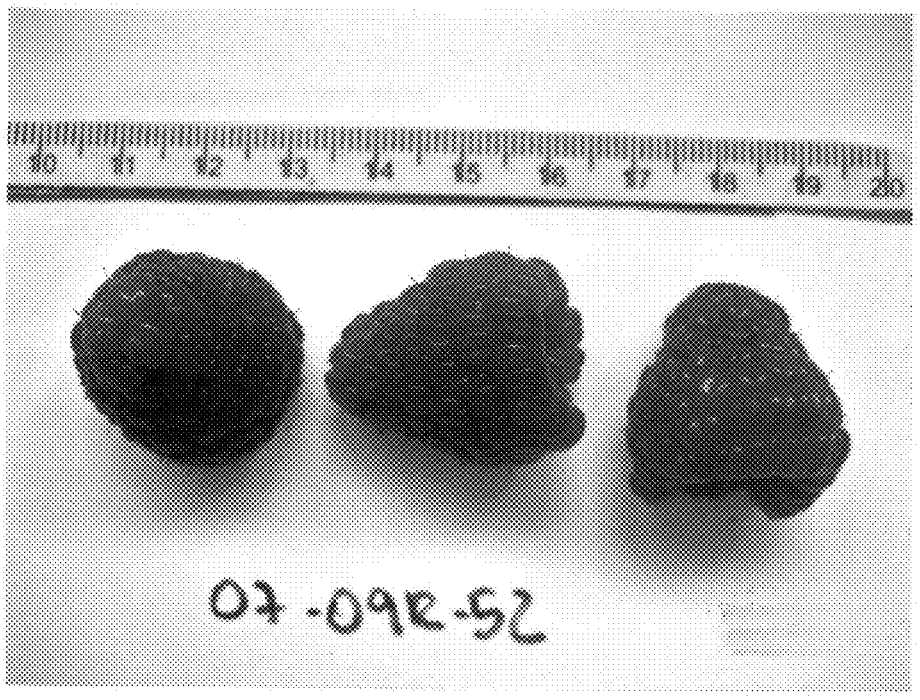
FIG. 12 and FIG. 13 show typical fruits of the new variety (designated 07.09R.52) with conical shape in lateral view, very strong glossiness and RHS red color (near 45 D to 46 B).
Figure 13:
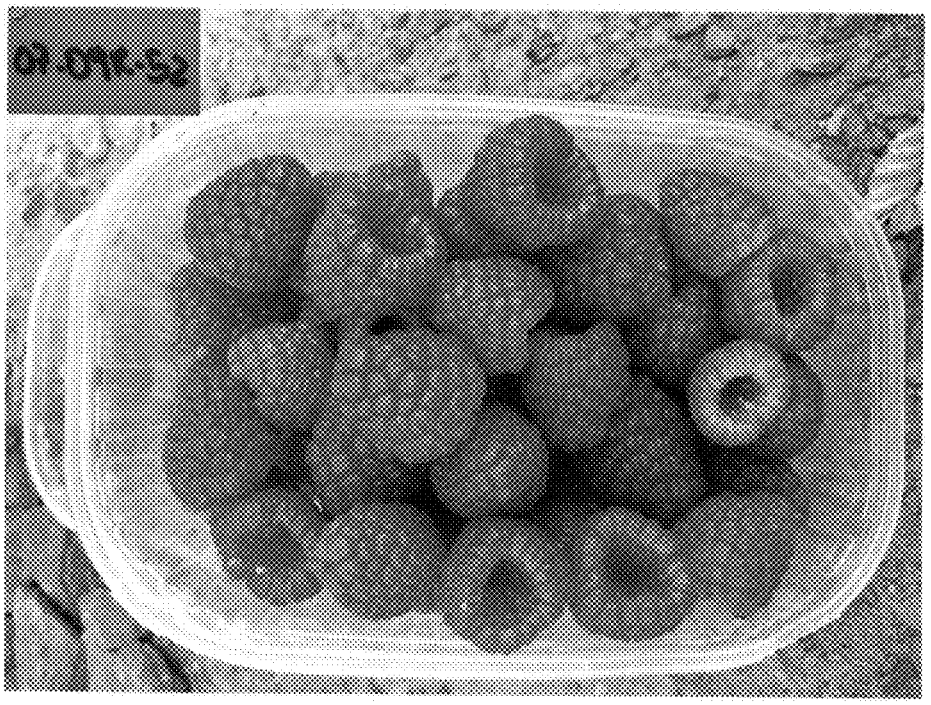
Figure 14:
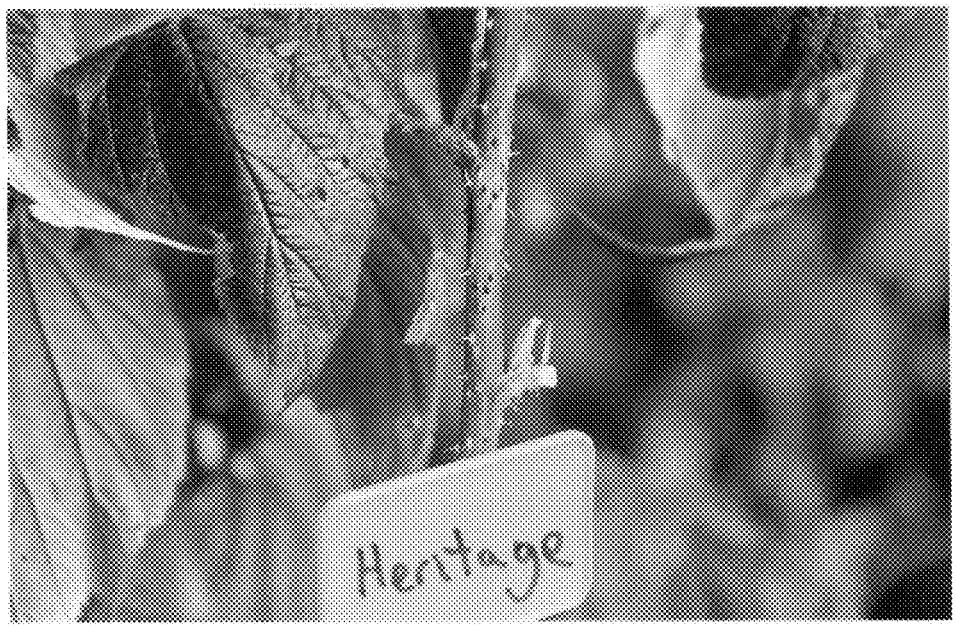
FIG. 14 shows the cane of raspberry variety 'Heritage' (Unpatented) with RHS greyed purple group color (near 185 C to 186 A) and high spines density.
Figure 15:
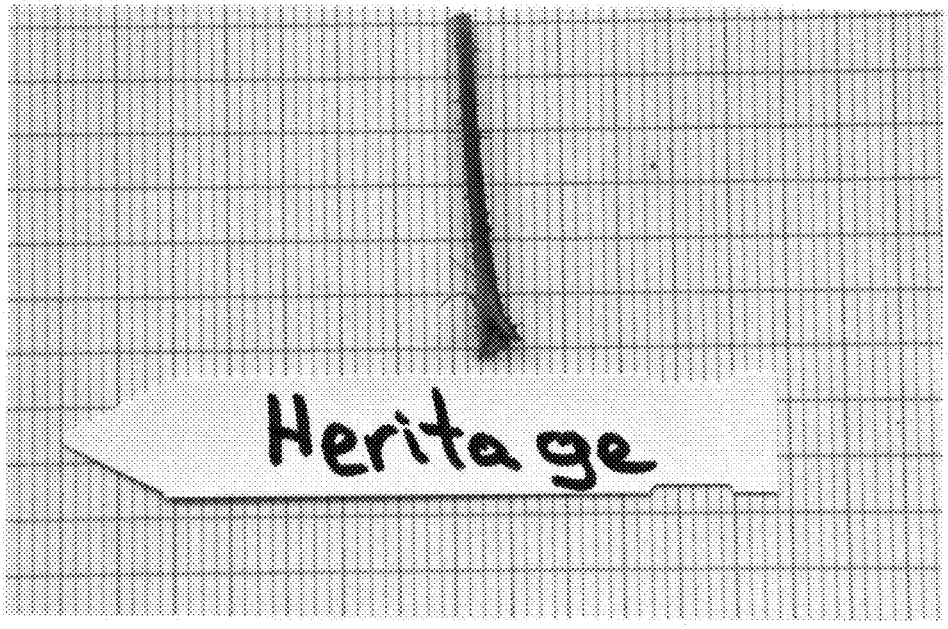
FIG. 15 shows the petiole of raspberry variety 'Heritage' (Unpatented) with RHS greyed red color (near 181 B to 181 A) and abundant spines.
Figure 16:
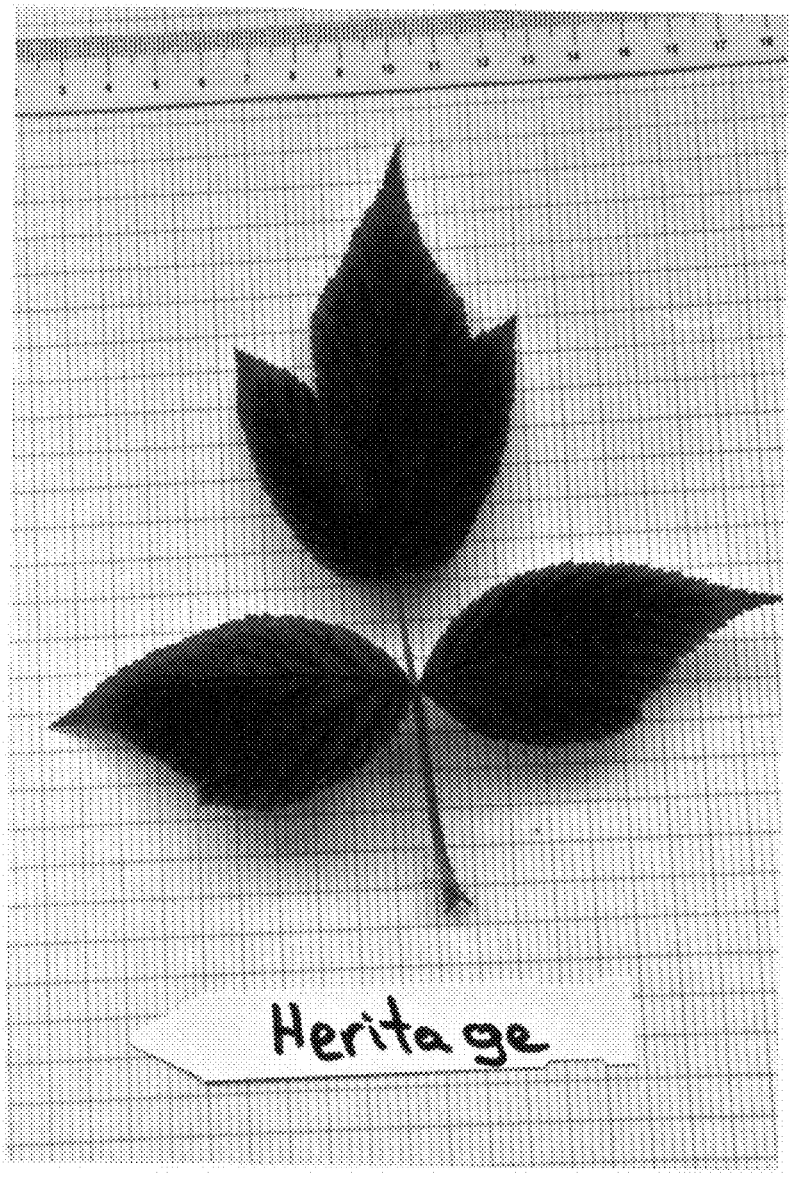
FIG. 16 shows a complete leaf of raspberry variety 'Heritage' (Unpatented) with a RHS yellow green group upperside color (near 147 A).
Figure 17:
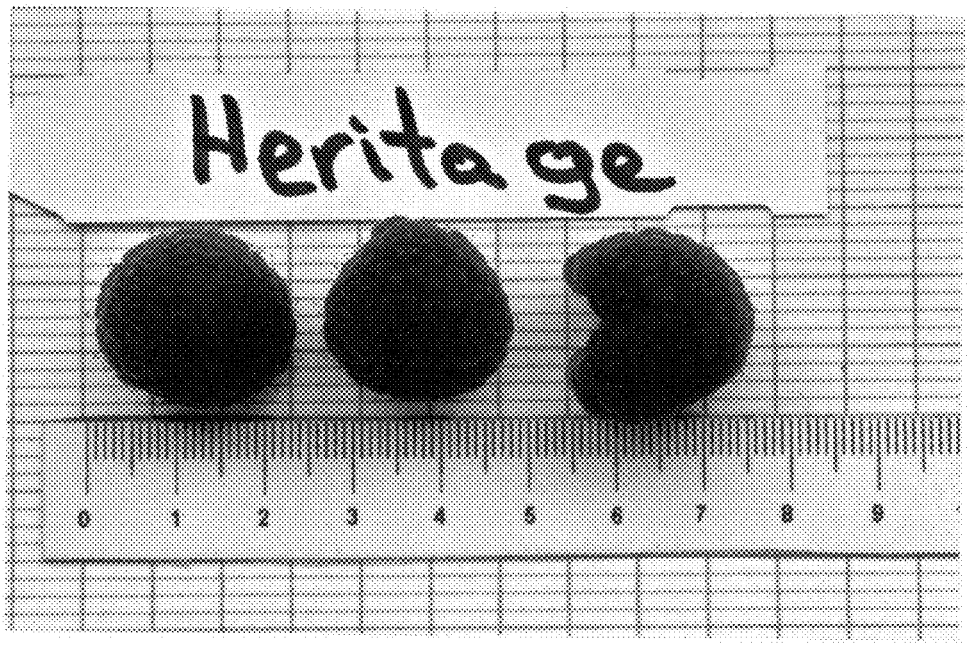
FIG. 17 shows typical fruits of raspberry variety 'Heritage' (Unpatented) with circular shape in lateral view and RHS red purple group color (near 59 A).

The following detailed description of the new variety is based upon observations taken of plants and fruits grown "underglass", i.e. undertunnel, in the farm of La Mogalla in Cartaya (Huelva), Spain, 7° W., 37° N., 45 feet elevation.

The following description is in accordance with UPOV terminology and the color terminology herein is in accordance with The Royal Horticultural Society Colour Chart (R.H.S.C.C.), 3$^{rd}$ edition published in 1995. The color descriptions and other phenotypical descriptions may deviate from the stated values and descriptions depending upon variation in environmental, seasonal, climatic and cultural conditions.

PROPAGATION

The new variety is principally propagated by way of root cuttings. Although propagation by root cuttings is presently preferred, other known methods of propagating raspberry plants may be used. Raspberries root and develop well after transplanting.

GENERAL

'Lupita' is propagated by root cuttings. It is a primocane variety with fruit production from October through December on primocanes and in the ensuing year beginning in April and ending in June. It is a self-fertile variety. It produces large quantity of pollen throughout the seasons and pollination is good.

Production: Plants described are from high elevation nursery in Segovia, Spain, 3° 59'W., 41° 22'N., 2742 feet elevation.

Trials pursued in Cartaya (Huelva), Spain.

Date of planting (two years): Jun. 22 , 2009 and Jun. 20, 2010.

Number of repetitions (every year): 3

Plants per repetition (every year): 120

Tables 1-4 below are expressed in grams per plant (g/plant). The tables represent the fruit quantity, in g/plant, picked up or accumulated. Fruits are classified in two ranks of quality:

$1^{st}$ quality: Fruits with the typical varietal fruit shape and harvested at optimal ripeness.

$2^{nd}$ quality: fruits with not well typical varietal fruit shape, not well formed and do not harvested at optimal ripeness.

Tables 1-4 express the accumulated yield and percentage distribution for each rank of quality.

TABLE 1

Accumulated production of 1st quality fruit (g/plant)

| Variety | Begins October to end December | Beginning in April ending in June | Total |
|---|---|---|---|
| 'LUPITA' | 807.12 | 635.27 | 1442.39 |
| 'RAFZAQU' (U.S. Plant Pat. No 19,512) | 946.58 | 610.29 | 1556.87 |

TABLE 2

Accumulated total yield: $1^{st}$ and $2^{nd}$ quality fruit (g/plant)

| Variety | $1^{st}$ + $2^{nd}$ quality Begins October to end December | $1^{st}$ + $2^{nd}$ Quality Beginning in April ending in June | Total |
|---|---|---|---|
| 'LUPITA' | 978.30 | 780.84 | 1759.14 |
| 'RAFZAQU' | 1164.22 | 835.14 | 1999.36 |

TABLE 3

Production from begins October through ending December of First Quality Fruit ($1^{st}$ quality) and Second Quality Fruit ($2^{nd}$ quality) in g/plant

| Variety | $1^{st}$ quality | $2^{nd}$ quality | TOTAL ($1^{st}$ quality + $2^{nd}$ quality) | % $2^{nd}$ quality |
|---|---|---|---|---|
| 'LUPITA' | 807.12 | 171.18 | 978.30 | 16.5 |
| 'RAFZAQU' | 946.58 | 217.64 | 1164.22 | 18.7 |

$$\%\ 2^{nd}\ \text{quality} = \frac{2^{nd}\ \text{quality}}{\text{TOTAL}} \times 100$$

TABLE 4

Production from end April through begins June of First Quality Fruit ($1^{st}$ quality) and Second Quality Fruit ($2^{nd}$ quality) in g/plant

| Variety | $1^{st}$ quality | $2^{nd}$ quality | TOTAL ($1^{st}$ quality + $2^{nd}$ quality) | % $2^{nd}$ quality |
|---|---|---|---|---|
| 'LUPITA' | 635.27 | 145.57 | 780.84 | 18.64 |
| 'RAFZAQU' | 610.29 | 224.85 | 835.14 | 26.92 |

$$\%\ 2^{nd}\ \text{quality} = \frac{2^{nd}\ \text{quality}}{\text{TOTAL}} \times 100$$

TABLE 5

Weight (g/fruit) in two production periods: October to December/April to June

| Variety | Begins October to end December | Beginning in April ending in June |
|---|---|---|
| 'LUPITA' | 7.0-6.0 | 7.5-5.5 |
| 'RAFZAQU' | 5.0-4.0 | 4.5-3.5 |

WEIGHT is shown as the average weight per fruit in First Quality Fruits.

The following additional information is provided to further describe the new variety.

Variety: 'Lupita'. Breeder Ref. 07.09R.52.

Classification: *Rubus idaeus* L.

Plants are grown in containers of 48 liters of capacity and they are observed and described during cultivar's primocane.

Plant:

*Habit*.—Arching.

*Vigor*.—Medium-high.

Cultivar's primocane cane:

*Length*.—About 180 to 200 cm.

*Diameter*.—About 50 to 70 cm.

*Texture*.—Smooth.

*Internode length*.—About 4.9 to 5.1 cm.

*Pubescence*.—Absent.

*Anthocyanin coloration of apex during rapid grow period*.—Absent.

*Cane color*.—RHS yellow green group color (near 144 C to 144 B) with RHS greyed red group pigmentation (near 178 D to 178 C).

Spines:
*Shape*.—Conical.
*Density*.—Medium sparse.
*Number/cm*.—About 3 to 4.
*Length*.—0.05 to 0.10 cm.
*Width*.—About 0.10 to 0.12 cm at the base.
*Apex*.—Hooked.
*Color*.—RHS greyed-purple group color (near 183 C to 183 B).
*Texture*.—Smooth.

Leaf:
*Type*.—Compound.
*Number of leaflets*.—3.
*Arrangement of lateral leaflets*.—Touching.
*Overlapping of lateral leaflets with terminal leaflet*.—Free.
*Upperside*.—RHS green group color (near 137 B to 137 A).
*Underside*.—RHS green group color (near 136 C to 136 B).
*Length of entire complete leaf*.—About 24.5 cm.
*Width of entire complete leaf*.—About 22 cm.
*Profile of leaflets in cross section*.—Straight.
*Relief between veins*.—Medium.

Lateral leaflet:
*Shape*.—Ovate.
*Length*.—About 12 cm. (Correction in line 7).
*Width*.—About 7.5 to 9.0 cm. (Correction in line 8).
*Shape of tip*.—Acuminate.
*Shape of base*.—Round to obtuse.
*Shape of margin*.—Serrate.
*Upperside rugosity*.—Weak to medium.
*Underside texture*.—Medium.
*Upperside coloration*.—RHS green group color (near 137 B to 137 A).
*Underside coloration*.—RHS green group color (near 136 C to 136 B).
*Venation pattern*.—Reticulate or penniveined.
*Upperside venation coloration*.—RHS green group color (near 138 C to 138 B).
*Underside venation coloration*.—RHS green group color (near 138 C to 138 B).

Terminal leaflet:
*Length/width ratio*.—Longer than broad.
*Length*.—About 25.5 cm.
*Width*.—About 13 cm.
*Cross section*.—Straight.
*Upperside*.—RHS green group color (near 137 B to 137 A).
*Underside*.—RHS green group color (near 136 C to 136 B).
*Shape of leaflet*.—Ovate.
*Shape of tip*.—Acuminate.
*Shape of base*.—Round to obtuse.
*Shape of margin*.—Serrate.
*Upperside rugosity*.—Weak to medium.
*Underside texture*.—Medium.
*Venation pattern*.—Reticulate or penniveined.
*Upperside venation coloration*.—RHS green group color (near 138 C to 138 B).
*Underside venation coloration*.—RHS green group color (near 138 C to 138 B).

Rachis:
*Length between the terminal leaflet and adjacent lateral leaflet*.—About 4.0 to 4.5 cm.
*Coloration*.—RHS green group color (near 138 C to 138 B).

Petiole:
*Color*.—RHS yellow green group color (near 144 C to 144 B) with RHS greyed red group pigmentation (near 178 D to 178 C).
*Length*.—About 7.5 to 8.0 cm.
*Length* (*rachis with petiolule*).—About 11.5 to 12.5 cm.
*Spines*.—Few.
*Diameter*.—About 3.0 to 4.0 mm in the petiolule and about 2.0 to 3.0 mm in the rachis.
*Texture*.—Smooth.

Stipule:
*Quantity per leaf*.—2.
*Shape*.—Horizontal. Tip attitude. downward.
*Length*.—About 1.10 to 1.30 cm.
*Width*.—Narrow. About 0.06 to 0.08 cm.
*Color* (*both surfaces*).—RHS yellow green group color (near 144 B to 144 A).

Flower:
*Diameter*.—About 2.1 to 2.3 cm.
*Pedicel color*.—RHS yellow green group color (near 144 C to 144 B).
*Depth*.—4.0 to 6.0 mm.

Flower bud:
*Shape*.—Broad conical.
*Diameter*.—About 7.0 to 9.0 mm.
*Length*.—About 8.0 to 10.0 mm.
*Color*.—RHS yellow-green group (near 144 C to 144 B).

Pedicel:
*Length*.—About 3.0 to 4.0 cm.
*Diameter*.—About 1.0 to 2.0 mm.
*Surface texture*.—Smooth.
*Density of spines*.—Very low.

Petal:
*Number of petals per flower*.—About 5 to 6.
*Shape*.—Narrow elliptique.
*Length*.—About 0.8 to 1.0 cm.
*Width*.—About 0.5 to 0.6 cm.
*Apex shape*.—Flat rounded.
*Base shape*.—Narrow.
*Margin*.—Smooth and regular.
*Texture*.—Smooth.
*Color*.—RHS white group color (near 155 C).

Peduncles:
*Length*.—About 12.0 to 14.0 cm.
*Diameter*.—About 3.0 to 4.0 mm.
*Surface texture*.—Smooth.
*Density of spines*.—Low.
*Color*.—RHS yellow-green group (near 144 C to 144 B).

Receptacle:
*Length*.—About 2.0 to 2.3 cm.
*Diameter*.—About 1.1 to 1.3 cm.
*Shape*.—Broad conical.
*Color*.—RHS orange-white group (near 159 C to 159 B).

Sepal:
*Number of sepals per flower*.—About 5 to 6.
*Shape*.—Triangular.
*Length*.—About 0.7 to 0.8 cm.

*Width*.—About 0.5 to 0.6 cm.
*Apex shape*.—Acuminate.
*Base shape*.—Large at the base forming the calyx.
*Margin*.—Smooth and regular.
*Texture*.—Smooth.
*Color*.—RHS green group color (near 142 D to 142 C).

Reproductive organs:
*Number of pistils per flower*.—About 95 to 100.
*Pistil length*.—About 0.3 to 0.4 cm.
*Ovary shape*.—Pyriform.
*Ovary length*.—Short.
*Ovary width*.—Narrow.
*Ovary color*.—RHS green group color (near 142 C to 142 B).
*Style length*.—About 0.20 to 0.25 cm.
*Style color*.—RHS white group color (near 155 C).
*Number of stamens per flower*.—About 85 to 90.
*Stamen length*.—About 0.5 to 0.6 cm.
*Stamen shape*.—Ovate.
*Stamen color*.—RHS green group color (near 142 D).
*Pollen amount*.—Abundant.
*Pollen color*.—RHS yellow green group color (near 153 C to 153 D).

Fruit:
*Shape*.—Broad conical.
*Length*.—About 2.3 to 2.6 cm.
*Width*.—About 2.5 to 2.7 cm.
*Color*.—RHS red group color (near 45 D to 46 B).
*Number of drupelets per fruit*.—About 100 to 115.
*Size of single drupelet*.—About 0.2 to 0.3 cm.
*Drupelet arrangement around the berry*.—Regular.
*Glossiness*.—Strong.
*Firmness*.—Firm.
*Adherence to plug*.—Medium.
*Diameter hollow center*.—About 2.0 to 2.5 cm.

Seeds:
*Number of seeds per drupelet*.—1.
*Shape*.—Slightly reniform.
*Color*.—RHS greyed-orange group (near 174 D to 174 C).
*Surface texture*.—Wrinkled.

Fruit bearing type: Both on previous year's cane in autumn and current year's cane in spring.

Fruiting lateral cane:
*Number of fruit per fruiting lateral cane*.—About 30 to 40 fruits.
*Average number of fruit per node*.—About 2 to 3 fruits.

General: The growing period in Huelva, Spain, where the observations on primocane production were made, is between about July 4 and July 14 of the following year. 'Lupita' is a primocane variety, with consistent fruit production from begins October through ending December on primocanes and in the ensuing year from the end of April through the beginning of June. After planting as aforesaid, plants are grown in raised beds under tunnel. Water and fertilizer were applied through drip irrigation.

Each year: Date of planting. — About June 20 in the farm of La Mogalla, in Cartaya (Huelva), Spain, about 7° W, 37° N, 45 feet elevation. Time of flowering data. — 10% flowering on primocane occurs about September 5. First mature fruits are about October 2 (15-20 g/plant), with a maximum production at the end October.

Storage qualities: 'Lupita' fruit maintains their quality characteristics when keeping them in a frigo chamber at temperatures of about 2° C. during 48 hours. The fruit's color remains substantially the same. Shelf life of 'Lupita' is good.

Use/market: The berries of 'Lupita' are suitable for consumption as fresh fruit. Also, they are amenable to processing.

Disease resistance: No particular sensitivity to any disease or pest has been observed for 'Lupita'.

I claim:

1. A new and distinct raspberry plant of the variety substantially as shown and described.

* * * * *